United States Patent
Enpuku et al.

(10) Patent No.: US 9,518,957 B2
(45) Date of Patent: Dec. 13, 2016

(54) MAGNETIC SIGNAL MEASURING APPARATUS AND MAGNETIC SIGNAL MEASURING METHOD

(71) Applicant: Hitachi, Ltd., Tokyo (JP)

(72) Inventors: Keiji Enpuku, Fukuoka (JP); Takako Mizoguchi, Tokyo (JP); Akihiko Kandori, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 179 days.

(21) Appl. No.: 14/607,187

(22) Filed: Jan. 28, 2015

(65) Prior Publication Data

US 2015/0247821 A1 Sep. 3, 2015

(30) Foreign Application Priority Data

Feb. 28, 2014 (JP) ................. 2014-039323

(51) Int. Cl.
G01N 27/72 (2006.01)
C12Q 1/00 (2006.01)
G01N 27/74 (2006.01)

(52) U.S. Cl.
CPC ............ *G01N 27/72* (2013.01); *G01N 27/745* (2013.01)

(58) Field of Classification Search
CPC .................................................... G01N 27/72
USPC ....................................................... 324/228
See application file for complete search history.

(56) References Cited

U.S. PATENT DOCUMENTS

2007/0212794 A1   9/2007  Tsukamoto et al.
2007/0254375 A1*  11/2007 Tsukamoto et al. .......... 436/149
2013/0078620 A1*  3/2013  Gandini et al. .................. 435/5

FOREIGN PATENT DOCUMENTS

JP   2004061144   2/2004
JP   2007240349   9/2007
JP   2009115529   5/2009

* cited by examiner

*Primary Examiner* — Bot Ledynh
(74) *Attorney, Agent, or Firm* — Mattingly & Malur, PC

(57) ABSTRACT

A magnetic signal measuring apparatus includes a first magnetic field applying unit that applies a first magnetic field to magnetic substances when a measured substance is binding to the magnetic substances, a second magnetic field applying unit that applies a second magnetic field to the magnetic substances to which the first magnetic field has been applied, and a SQUID that measures a magnetic signal derived from the magnetic substances. The first magnetic field has an intensity of such a degree that the magnetic substances do not flocculate with each other and such a degree that directions of magnetic moments in the magnetic substances can be aligned with each other. The second magnetic field has an intensity of such a degree that the magnetic substances do not flocculate with each other and such a degree that a magnetic signal can be obtained from the magnetic substances.

8 Claims, 9 Drawing Sheets

COMPARATIVE EXAMPLE

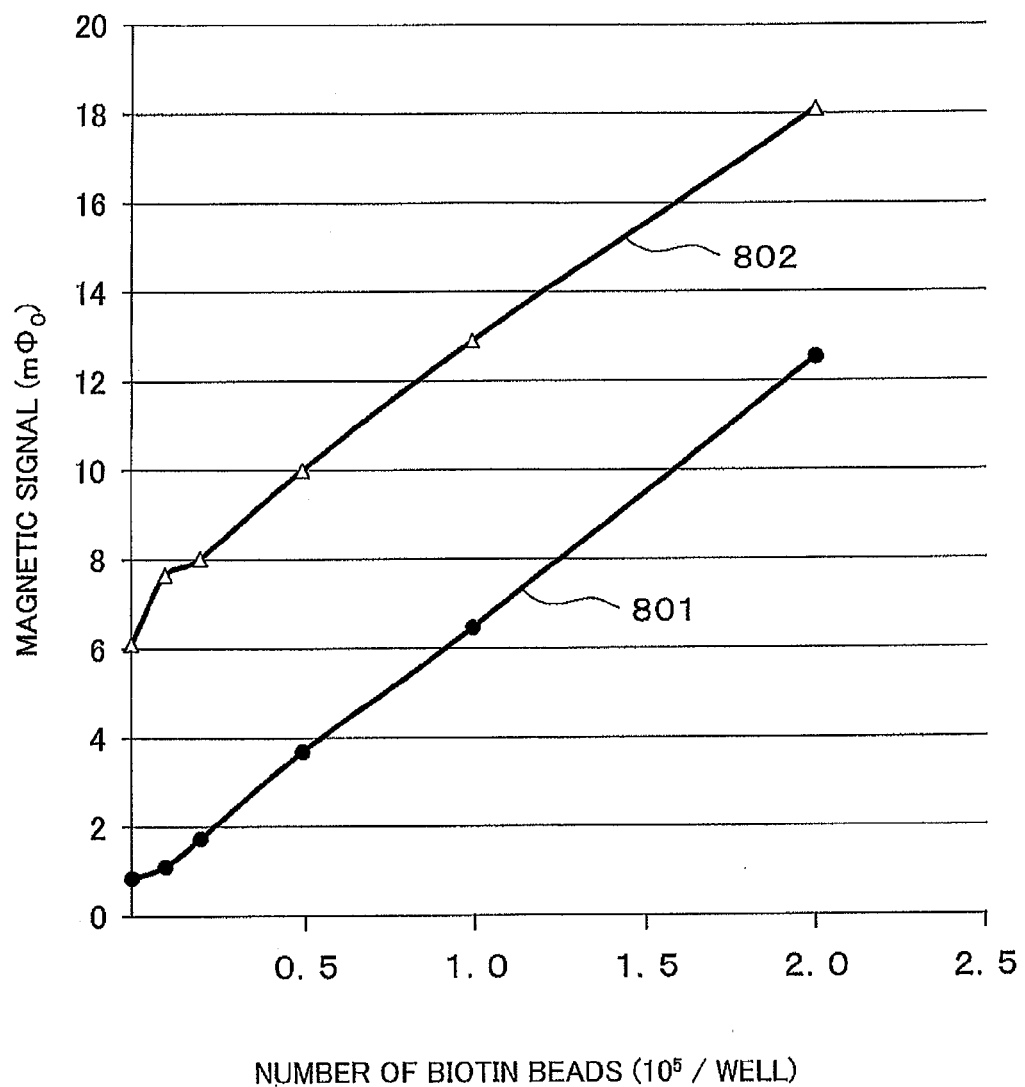

FIG.9A
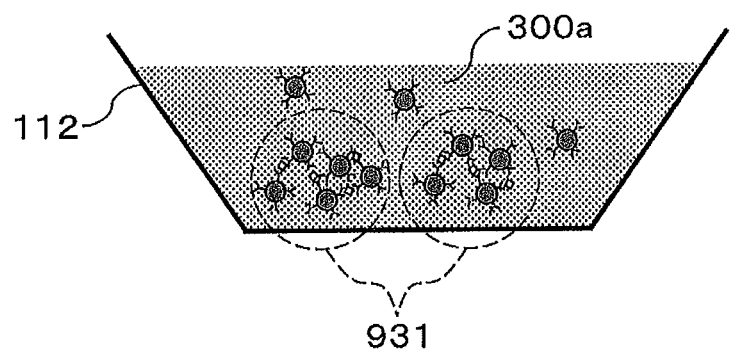
FIG.9B
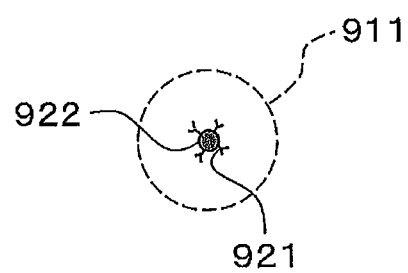
FIG.9C      FIG.9D
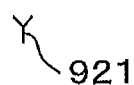      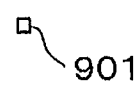

MAGNETIC SIGNAL MEASURING APPARATUS AND MAGNETIC SIGNAL MEASURING METHOD

CROSS-REFERENCE TO RELATED APPLICATION

This application is based upon and claims the benefit of priority to the Japanese Patent Application No. 2014-039323, filed on Feb. 28, 2014, the entire contents of which are incorporated herein by reference.

BACKGROUND OF THE INVENTION

1. Field of the Invention

The present invention relates to a technique for a magnetic signal measuring apparatus and a magnetic signal measuring method which measure a magnetic signal derived from a magnetic substance binding to a substance to be measured (for convenience, hereinafter referred to as a measured substance) in a liquid.

2. Description of the Related Art

In recent years, a technique for an immunological test has made rapid progress in diagnosis of infection, cancer, allergy and the like. The immunological test is a technique of detecting and quantifying a measured substance in a biological body based on a specific binding reaction between an antigen and an antibody. The measured substance in the immunological test is mainly a protein and is specifically a pathogenic microorganism, an antigen derived from foods, an immunoglobulin, a hormone, a tumor marker or the like. In the immunological test, one or several types of antibodies whose binding-capacity to a measured substance is preliminarily known are used to detect the measured substance in the biological body based on the presence or absence of binding between the measured substance and the antibodies and/or the degree of binding therebetween.

Conventionally, an optical immunological test is used in which an antibody whose binding capacity to a measured substance is known is labeled with a luminescent substance, a fluorescent substance, enzyme or the like and the degree of binding between the antibody and the measured substance is optically detected. The antibody labeled in the method of such an optical immunological test is referred to as a labeled antibody. For example, an FTA (Fluorescent Treponemal Antibody test), an EIA (Enzyme ImmunoAssay) and the like are known as representative methods.

Herein, in most of optical immunological tests, when labeled antibodies which have not bound to measured substances remain, a non-specific signal is detected from a luminescent substance or a fluorescent substance. To cope with this, a process of flushing and removing redundant labeled antibodies is required.

On the other hand, unlike the optical immunological test, a technique is known as a magnetic immunological test, which detects a measured substance using a magnetic method such as described in Patent Document 1 (Japanese Patent No. 4676361) and Patent Document 2 (Japanese Patent No. 5189825). In the magnetic immunological test, an antibody is first labeled with a magnetic particle. Thus, the magnetic particle labeled by the antibody is referred to as a magnetic particle antibody. Then, a magnetic signal due to a binding reaction between the measured substance and the magnetic particle antibody is detected by a magnetic sensor.

For example, in a case of using a SQUID (Superconducting QUantum Interference Device) magnetic sensor, a sample is produced in which measured substances fixed onto a bead carrier having a particle diameter of micron scale and magnetic particle antibodies are bound to each other in a solution. Then, an external direct-current (DC) magnetic field is applied to the sample to magnetize the magnetic particle antibodies. Next, when the external DC magnetic field is shut off, the magnetic particle antibody which has bound to the measured substance more increases in size than the magnetic particle antibody which has not bound to the measured substance and accordingly a rotational Brownian motion of the former magnetic particle antibody becomes slow. This causes the magnetic particle antibody binding to the measured substance to have remanent magnetism, thereby allowing a magnetic signal derived from the magnetic particle antibody to be detected.

On the other hand, the magnetic particle antibody not having bound to the measured substance also exists in the solution. The magnetic particle antibody not having bound to the measured substance has a smaller particle diameter because it exists alone, and thus a rotational Brownian motion thereof becomes rapid. Accordingly, as for the magnetic particle antibody not binding to the measured substance, the direction of the magnetic moment thereof easily becomes random and thus there is no remanent magnetism therein. This makes the magnetic particle antibody not binding to the measured substance unable to be detected as a magnetic signal.

Thus, the magnetic immunological test has an advantage in that it requires no process of flushing and removing magnetic particle antibodies, because it utilizes the difference of remanent magnetic property of the magnetic particle antibodies, which is influenced by the presence or absence of binding to the measured substance.

The magnetic immunological test as described above requires a process of preliminarily magnetizing magnetic particle antibodies, prior to measuring a magnetic signal. The intensity of a magnetic signal detected from the magnetic particle antibody depends on the intensity of an externally-applied magnetic field and the density of the magnetic moments of the magnetic particle antibodies. Accordingly, in the magnetic immunological test, the more intense the magnetic field becomes and the higher the density of the magnetic moments becomes, the higher the intensity of a magnetic signal to be measured becomes. As an example of application of this principle, there is a method such as described in Patent Document 3 (Japanese Patent Application Publication No. 2004-061144), in which, after an antigen-antibody reaction process, a sample is dried with a magnetic field of 0.5 to 500 gauss being applied. In this method, drying the sample in the magnetic field makes it possible to align the directions of the magnetic moments in the magnetic particle antibodies with each other and to increase the density of the magnetic moments. Thus, according to the method described in Patent Document 3, an intense magnetic signal can be obtained.

However, the method described in Patent Document 3 requires a process of preliminarily flushing and removing redundant magnetic particle antibodies not binding to measured substances. This is because, when redundant magnetic particle antibodies remain in drying the sample in the magnetic field, a blank value increases. The blank value means a value of a magnetic signal detected even where the abundance of the measured substances is "0". Also, in general, since an immunological test requires a short-time and efficient test, a drying process requiring a long time, such as encountered in the method described in Patent Document 3, is not suitable for such an immunological test.

On the other hand, the methods described in Patent Document 1 and Patent Document 2 use a liquid sample thereby enabling a short-time test, as compared to the method described in Patent Document 3 in which the sample is dried. However, in the process of preliminarily applying an external DC magnetic field to the sample to magnetize the magnetic particle antibodies, a phenomenon is caused in some cases in which redundant magnetic particle antibodies not binding to measured substances flocculate non-specifically. This is because the externally-applied magnetic field is intensified for the purpose of intensifying remanent magnetism in the magnetic particle antibodies to obtain an intense magnetic signal. Thus, when non-specific flocculation of the magnetic particle antibodies is caused, a clump of magnetic particle antibodies is produced in which the directions of magnetic moments in the magnetic particle antibodies are aligned with each other and the density of the magnetic moments is also increased. Consequently, a problem occurs in that a magnetic signal is generated from such a clump of magnetic particle antibodies to increase a blank value.

SUMMARY OF THE INVENTION

The present invention has been made in view of the above background and an object thereof is to provide a magnetic signal measuring apparatus and a magnetic signal measuring method which can decrease a blank value in a magnetic measurement.

In order to solve the above problems, the present invention is characterized in that a magnetic field is twice applied to a sample containing magnetic substances; a first magnetic field has an intensity of such a degree that the magnetic substances do not flocculate with each other and such a degree that directions of magnetic moments in the magnetic substances can be aligned with each other; and a second magnetic field has an intensity of such a degree that the magnetic substances do not flocculate with each other and such a degree that a magnetic signal is allowed to be obtained.

According to one aspect of the present invention, there is provided a magnetic signal measuring apparatus including: a first magnetic field applying unit that is arranged to apply a first magnetic field to a sample in which a plurality of magnetic substances and a measured substance able to bind to the magnetic substances are mixed together in an unbound state, the first magnetic field having an intensity of such a degree that the magnetic substances do not flocculate with each other and such a degree that directions of magnetic moments in the magnetic substances can be aligned with each other; a second magnetic field applying unit that is arranged to apply a second magnetic field to the magnetic substances to which the first magnetic field has been applied, the second magnetic field having an intensity of such a degree that the magnetic substances do not flocculate with each other and such a degree that a magnetic signal can be obtained from the magnetic substances; and a measurement unit that is arranged to measure the magnetic signal derived from the magnetic substances.

According to another aspect of the present invention, there is provided a magnetic signal measuring method implemented by a magnetic signal measuring apparatus that measures a magnetic signal derived from a plurality of magnetic substances binding to a measured substance, the magnetic signal measuring method including: applying a first magnetic field to a sample in which the magnetic substances and the measured substance are mixed together in an unbound state, the first magnetic field having an intensity of such a degree that the magnetic substances do not flocculate with each other and such a degree that directions of magnetic moments in the magnetic substances can be aligned with each other; applying a second magnetic field to the magnetic substances to which the first magnetic field has been applied, the second magnetic field having an intensity of such a degree that the magnetic substances do not flocculate with each other and such a degree that the magnetic signal can be obtained from the magnetic substances; and measuring the magnetic signal derived from the magnetic substances.

According to the present invention, a blank value in a magnetic measurement can be decreased.

BRIEF DESCRIPTION OF THE DRAWINGS

FIG. 8 is a graph representing measured results based on each of measuring methods.

FIGS. 9A to 9D are views schematically showing a reaction in a modified example in which magnetic particle antibodies are mutually flocculated with measured substances lying therebetween.

EMBODIMENT OF THE INVENTION

Hereinafter, the mode for carrying out the present invention (hereinafter referred to as "embodiment") will be described in detail with reference to the drawings as appropriate.

[Magnetic Signal Measuring Apparatus]

Figure 1A:
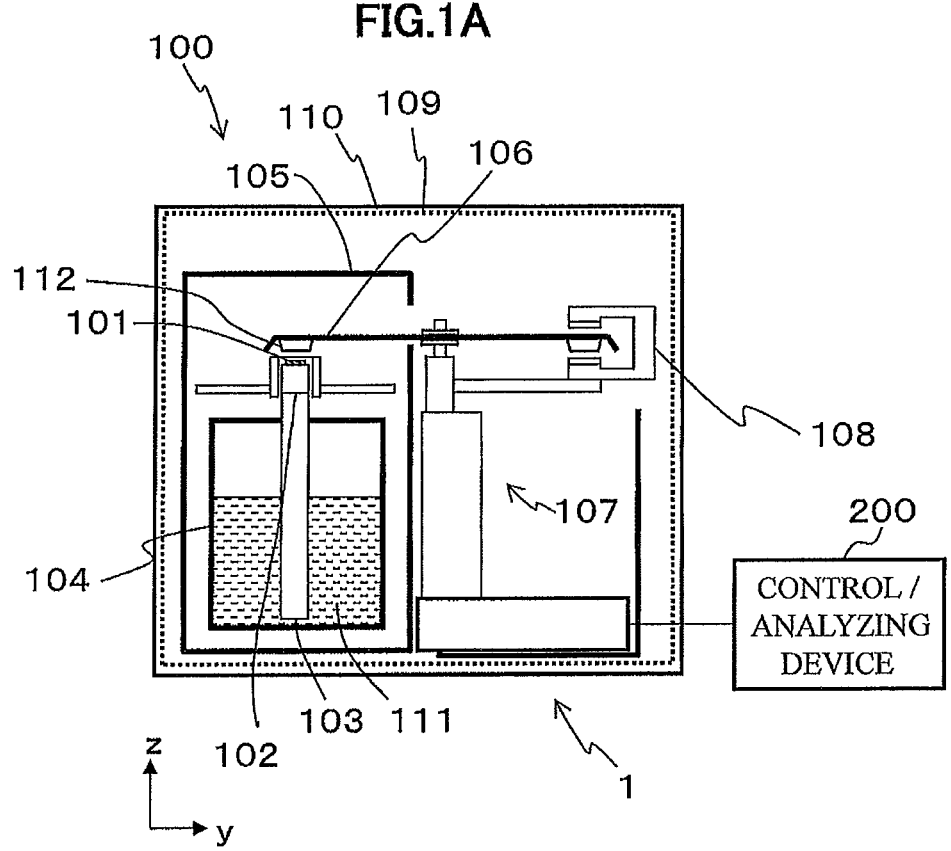
FIGS. 1A and 1B are views showing a configuration example of a magnetic signal measuring system according to an embodiment of the present invention.
Figure 1B:
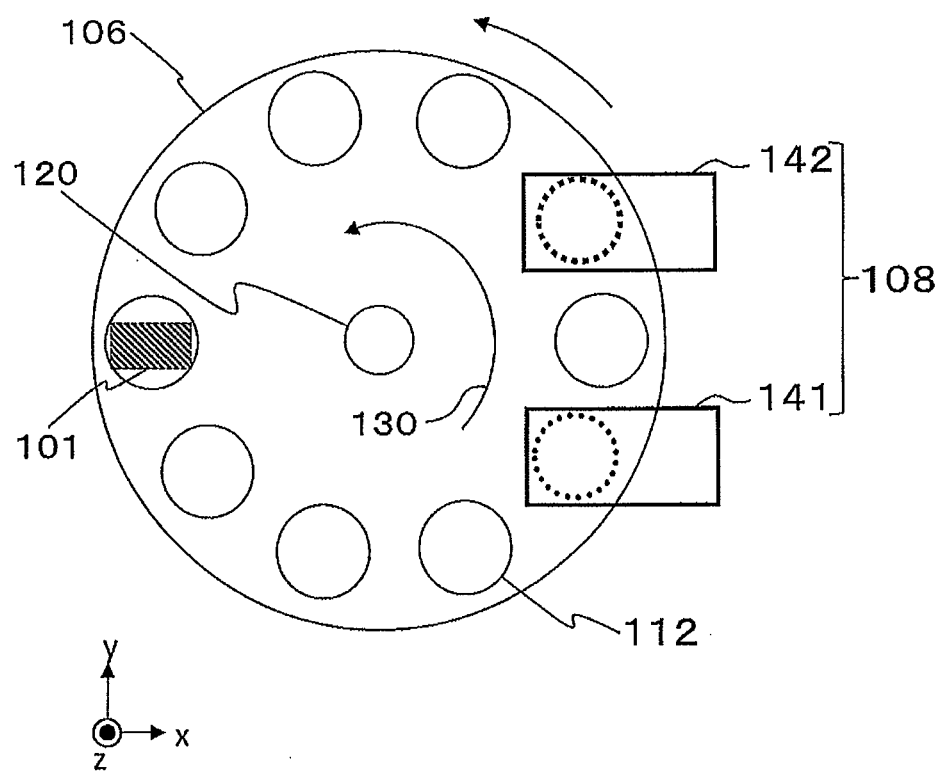

FIGS. 1A and 1B are views showing a configuration example of a magnetic signal measuring system according to an embodiment of the present invention. FIG. 1A shows a side overview of a magnetic signal measuring apparatus and a control/analyzing device, and FIG. 1B shows a top view of a sample container.

In a magnetic signal measuring system 1, a magnetic signal measuring apparatus 100 includes a plane type SQUID sensor (hereinafter referred to as a SQUID 101). The magnetic signal measuring apparatus 100 also includes a sapphire rod 102 for holding thereon the SQUID 101 and a copper rod 103. In addition, the magnetic signal measuring apparatus 100 includes a cooling container 104 for cooling the SQUID 101. Moreover, the magnetic signal measuring apparatus 100 includes a magnetic shield 105 which accommodates the SQUID 101 and the cooling container 104. The magnetic signal measuring apparatus 100 also includes a sample container 106. The sample container 106 has a well 112 for holding therein a liquid sample in which a magnetic particle antibody (magnetic substance) and a measured substance are bound to each other in a solution. Moreover, the magnetic signal measuring apparatus 100 includes a rotating mechanism 107 which is adapted to support and rotate the sample container 106. Furthermore, the magnetic signal measuring apparatus 100 includes a magnetic field applying unit 108 which is adapted to apply a magnetic field to the liquid sample in the sample container 106. The magnetic field applying unit 108 will be described later. The magnetic signal measuring apparatus 100 also includes an electromagnetic shield 109 and a magnetic shield 110 which accommodate each of the above members and the above mechanism.

The cooling container 104 is filled up with liquid nitrogen 111 and the copper rod 103 is immersed in the liquid nitrogen 111. The copper rod 103 and the sapphire rod 102 are connected to each other. The SQUID 101 which is attached to the upper surface of the sapphire rod 102 is indirectly cooled with the liquid nitrogen 111 via the copper rod 103 and the sapphire rod 102. The SQUID 101 cooled functions as a magnetic sensor to detect a magnetic signal generated from the magnetic particle antibody in the liquid sample.

The sample container 106 which holds the liquid sample is rotated by the rotating mechanism 107 in a process of detecting the magnetic signal. After the liquid sample is magnetized by the magnetic field applying unit 108 which applies a magnetic field, the liquid sample passes above the SQUID 101 by the rotation of the sample container 106. The amount of change of a magnetic field generated when the liquid sample in the well 112 passes above the SQUID 101 is detected by the SQUID 101 as the amount of magnetism originating from the liquid sample. The magnetic field applying unit 108 which applies a magnetic field includes a mechanism which applies a DC magnetic field with an electromagnet coil.

A control/analyzing device 200 is a device adapted to rotate the sample container 106 in the magnetic signal measuring apparatus 100 and to receive and analyze a magnetic signal measured by the SQUID 101.

As shown in FIG. 1B, when the sample container 106 which accommodates the liquid sample is rotated, the well 112 is moved. This allows the well 112 to pass above the magnetic field applying unit 108 and the SQUID 101.

The sample container 106 has a disc-like form as shown in FIG. 1B, and is made of a non-magnetic material such as resin. The sample container 106 has in the center thereof a hole 120 for use in fixing the sample container 106 to the rotating mechanism 107, and has the wells 112 at ten spots in the periphery thereof. The rotating mechanism 107 allows the sample container 106 to be rotated in the direction indicated by an arrow mark 130. It is desirable that the rotational speed is constant, but the sample container 106 may have an intermittent rotation which includes a stop for a given period of time.

As shown in FIG. 1B, the well 112 passes through a first magnetic field applying unit 141 and a second magnetic field applying unit 142 which constitute the magnetic field applying unit 108, at two given points. This allows a first magnetic field and a second magnetic field to be applied to the liquid sample in the well 112. The well 112 also passes above the SQUID 101, at one given point. When the well 112 passes above the SQUID 101, a magnetic signal is measured from the liquid sample in the well 112. Note that the number of the well 112 is not limited to ten.

Figure 2:
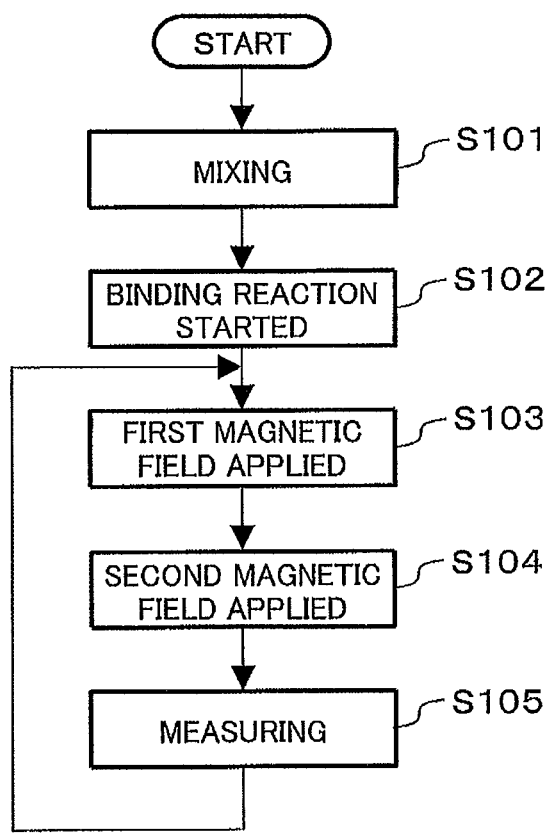
FIG. 2 is a flowchart representing detailed steps of an immunological test method in the present embodiment.

FIG. 2 is a flowchart representing detailed steps of an immunological test method in the present embodiment. Reference to FIGS. 1A and 1B will be made as appropriate.

In the magnetic immunological test in the present embodiment, first, mixing of measured substances and magnetic particle antibodies is performed in a solution filled in the well 112 (step S101) to produce a liquid sample.

Then, a binding reaction between the measured substances and the magnetic particle antibodies is started (step S102). For example, when the measured substances are each an antigen, the binding reaction becomes one generally called an antigen-antibody reaction and thus a specific binding reaction between the antigens and the antibodies is performed. In general, this binding reaction continues to be performed until a sequence of measurement processing is finished.

Next, the sample container 106 is rotated to cause the liquid sample to pass through the first magnetic field applying unit 141, thereby allowing the first magnetic field to be applied to the liquid sample under the binding reaction (step S103). The intensity of the first magnetic field is, although described later, an intensity of such a degree that magnetic particle antibodies (magnetic particles) which have not bound to the measured substances do not flocculate with each other.

After the liquid sample passing through the first magnetic field applying unit 141, the sample container 106 is further rotated to cause the liquid sample to move out of the first magnetic field applying unit 141. This allows the first magnetic field which has been applied to the liquid sample to be shut off.

Note that, after the binding reaction is started at step S102, in order to wait for the binding reaction progressing to some extent, it is preferable that step S103 is started after a lapse of about several minutes to several tens of minutes from the start of the binding reaction.

Subsequently, the sample container 106 is further rotated to cause the liquid sample to pass through the second magnetic field applying unit 142, thereby allowing the second magnetic field to be applied to the liquid sample (step S104). The intensity of the second magnetic field is, although described later, an intensity of such a degree that magnetic particle antibodies (magnetic particles) which have not bound to the measured substances do not flocculate with each other, and an intensity which is higher than the intensity of the first magnetic field. Note that in the present embodiment, although the second magnetic field is applied while the binding reaction is performed, the second magnetic field may be applied after the binding reaction is stopped.

After the liquid sample passing through the second magnetic field applying unit 142, the sample container 106 is further rotated to cause the liquid sample to move out of the second magnetic field applying unit 142. This allows the second magnetic field which has been applied to the liquid sample to be shut off.

Then, when the sample container 106 is further rotated to cause the liquid sample to pass above the SQUID 101, a magnetic signal for the liquid sample is measured by the SQUID 101 (step S105). Thereafter, the processings at steps S103 to S105 are repeated.

Note that the time required for the sample container 106 to make one revolution is about several tens of seconds.

That is, for one liquid sample, the application of the first magnetic field, the application of the second magnetic field, and the measurement of the magnetic signal are performed more than once. Then, the control/analyzing device 200 signal-averages results of the measurement of the magnetic signal performed more than once. This makes it possible to improve an S/N (signal-to-noise) ratio.

Figure 3A:
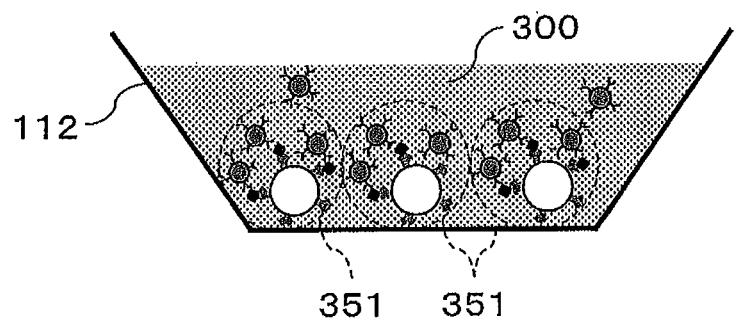
FIGS. 3A to 3F are views showing a detailed composition of a liquid sample.
Figure 3B:
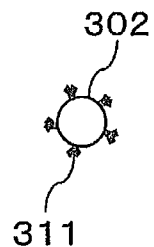
Figure 3C:
Figure 3D:
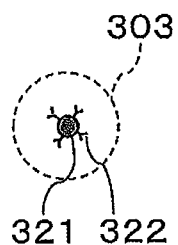
Figure 3E:
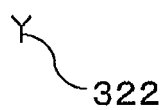
Figure 3F:

FIGS. 3A to 3F are views showing a detailed composition of a liquid sample. FIG. 3A is a schematic view showing a state within the well 112; FIG. 3B is an enlarged schematic view showing a bead carrier to which a first antibody is fixed; and FIG. 3C is an enlarged schematic view showing the first antibody. Moreover, FIG. 3D is an enlarged schematic view showing a magnetic particle antibody; FIG. 3E is an enlarged schematic view showing a second antibody; and FIG. 3F is an enlarged schematic view showing an antigen.

As shown in FIG. 3A, a liquid sample 300 is accommodated in the well 112, in which an antigen 301, a bead carrier 302 (see FIG. 3B) to which a first antibody 311 is fixed, and a magnetic particle antibody 303 are mixed together. As shown in FIG. 3B, the first antibody 311 able to bind specifically to the antigen 301 is fixed onto the bead carrier 302. Moreover, the magnetic particle antibody 303 has a composition in which a second antibody 322 able to bind specifically to the antigen 301 is fixed to the surface of a magnetic particle (magnetic substance) 321. In the binding reaction started at step S102 in FIG. 2, respective bindings between the first antibody 311 fixed onto the bead carrier 302 and the antigen 301, and between the second antibody 322 in the magnetic particle antibody 303 and the antigen 301, are performed (sandwich binding reaction) to form a complex 351 containing the antigens and the antibodies.

Note that even where the second antibody 332 contains a recognition site for the antigen 301 and a complex containing the first antibody 311 and the antigen 301 is formed, when the magnetic particle antibodies 303 excessively exist, redundant magnetic particle antibodies 303 do not form the complex 351 and exist with a state of an elementary substance, respectively.

Comparative Example

Figure 4A:
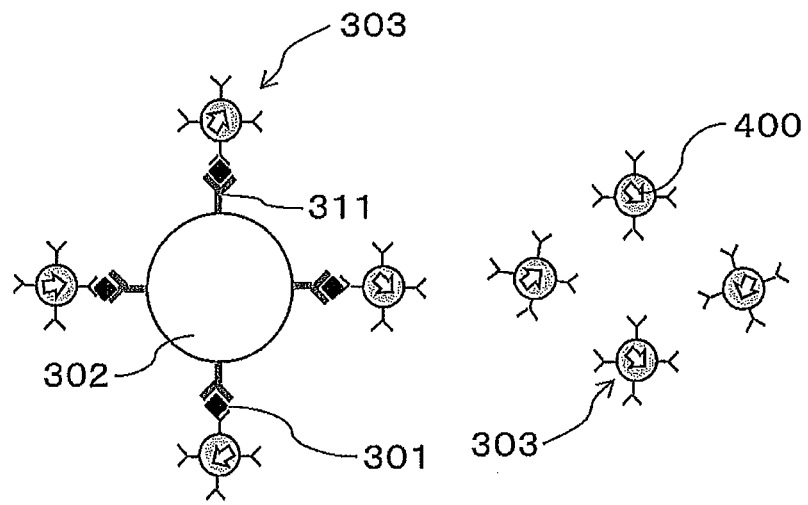
FIGS. 4A and 4B are views schematically showing a phenomenon caused by applying a magnetic field only once to a magnetic particle antibody, as a comparative example.
Figure 4B:
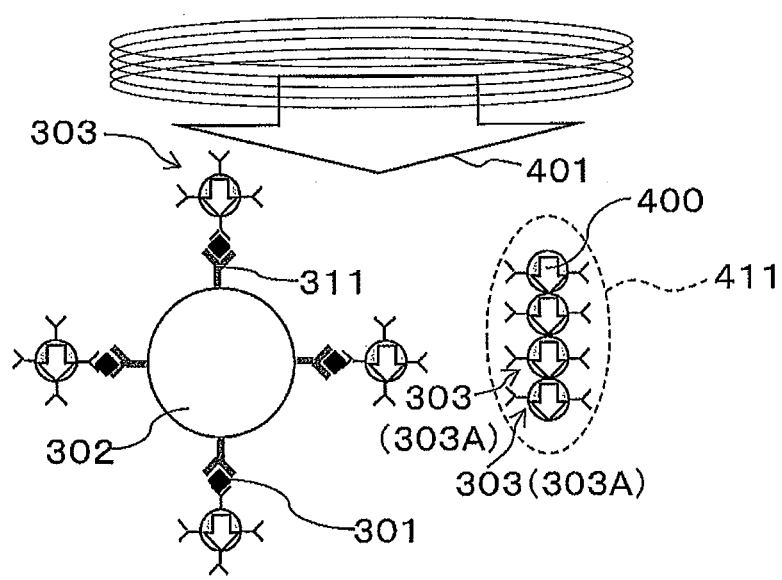

FIGS. 4A and 4B are views schematically showing a phenomenon caused by applying a magnetic field only once to a magnetic particle antibody, as a comparative example. Note that in FIGS. 4A and 4B, and FIGS. 5A and 5B, the same element as that shown in FIGS. 3A to 3F is given the same reference sign and thus explanation thereof will be omitted.

FIG. 4A shows a case where a binding reaction between the antigen 301 and the magnetic particle antibody 303 is performed with no magnetic field applied.

Since the magnetic particle antibodies 303 rotates by Brownian motion in the solution, as shown in FIG. 4A, a binding reaction between the antigens 301 and the magnetic particle antibodies 303 is performed with a state in which directions of magnetic moments 400 in the magnetic particle antibodies 303 (magnetic particles 321) become random. Thus in the state in which the directions of the magnetic moments 400 in the magnetic particle antibodies 303 become random, magnetic signals which emanate from the respective magnetic particle antibodies 303 cancel each other out to thereby cause a magnetic signal emanating from all the magnetic particle antibodies 303 to be decreased.

To cope with this, as shown in FIG. 4B, when an intense magnetic field 401 is applied to the magnetic particle antibodies 303 to forcibly align the magnetic moments 400 in the magnetic particle antibodies 303 (magnetic particles 321) with each other in one direction. Thus, aligning the magnetic moments 400 in the magnetic particle antibodies 303 with each other in one direction makes it possible to intensify the magnetic signal. However, as a result, no complex 351 is formed and redundant magnetic particle antibodies 303A that exist with a state of an elementary substance, respectively, are also strongly magnetized. This causes the redundant magnetic particle antibodies 303A to flocculate with each other as indicated by reference sign 411 in FIG. 4B. Consequently, a phenomenon is caused in which a magnetic signal derived from the flocculating magnetic particle antibodies 303A is generated, which leads to an increase in a blank value.

Present Embodiment

Figure 5A:
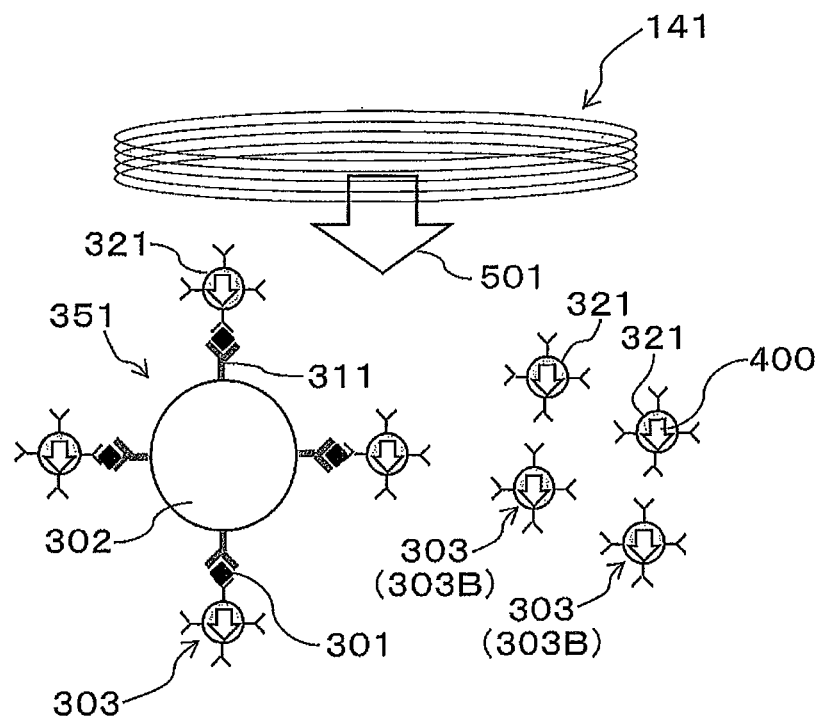
FIGS. 5A and 5B are views schematically showing a phenomenon caused by applying a magnetic field twice to a magnetic particle antibody, using the method according to the present embodiment.
Figure 5B:
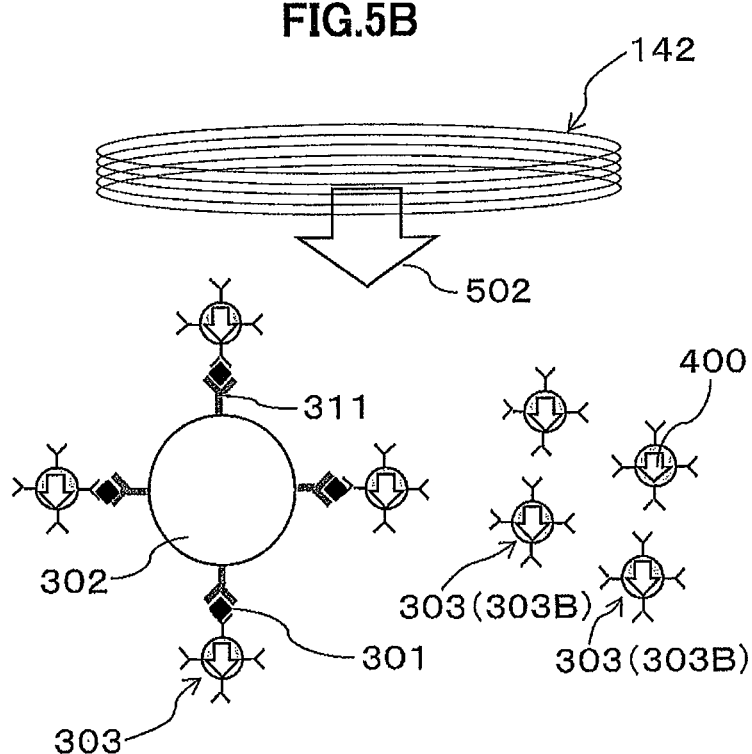

FIGS. 5A and 5B are views schematically showing a phenomenon caused by applying a magnetic field twice to a magnetic particle antibody, using the method according to the present embodiment.

As shown in FIG. 5A, the first magnetic field applying unit 141 applies the first magnetic field 501 to the magnetic particle antibodies 303 while the antigen-antibody reaction (binding reaction) is performed, at step S103 in FIG. 2 in the present embodiment. The first magnetic field 501 is intended to align the directions of the magnetic moments 400 in the magnetic particle antibodies 303 (magnetic particles 321) with each other and thus has an intensity of such a degree as to prevent a rotational Brownian motion and not to cause flocculation of the magnetic particle antibodies 303. That is, the intensity of the first magnetic field 501 is an intensity of such a degree as not to cause flocculation of the magnetic particle antibodies 303, and an intensity of such a degree as to allow the directions of the magnetic moments 400 in the magnetic particle antibodies 303 to align with each other.

The binding reaction is performed under conditions that the first magnetic field 501 is applied to the magnetic particle antibodies 303, thereby allowing the complex 351 to be formed with a state in which the directions of the magnetic moments 400 in the magnetic particle antibodies 303 are aligned with each other. The magnetic particle antibodies 303 are brought into the state in which the directions of the magnetic moments 400 are aligned with each other, thereby making it possible, in a magnetic signal measurement to be performed later, to facilitate the measurement of a magnetic signal and improve a measurement accuracy of the magnetic signal.

With the binding reaction, redundant magnetic particle antibodies 303B also exist. As shown in FIG. 5A, the redundant magnetic particle antibodies 303B do not form the complex 351 and exist with a state of an elementary substance, respectively.

Then, as shown in FIG. 5B, the second magnetic field applying unit 142 applies the second magnetic field 502 to the magnetic particle antibodies 303 each binding to the antigen 301 in the complex 351, at step S104 in FIG. 2, and magnetizes the magnetic particle antibodies 303 (magnetic particles 321). The intensity of the second magnetic field 502 is an intensity of such a degree as not to cause flocculation of the magnetic particle antibodies 303, and an intensity of such a degree as to allow the SQUID 101 to receive a magnetic signal. Moreover, the intensity of the second magnetic field 502 is higher than the intensity of the first magnetic field 501.

Under application of the second magnetic field 501, no complex 351 is formed and the redundant magnetic particle antibodies 303B each existing as the elementary substance are magnetized, but the redundant magnetic particle antibodies 303B do not flocculate with each other because the second magnetic field 502 has an intensity of such a degree as not to cause flocculation of the magnetic particle antibodies 303. Consequently, a blank value which is detected due to flocculation does not increase.

Hereinafter, conditions for the first magnetic field 501 and the second magnetic field 502 will be described in detail with reference to FIGS. 1A and 1B, FIGS. 3A to 3F, and FIGS. 5A and 5B as appropriate.

As described above, the first magnetic field 501 to be applied in the magnetic signal measuring apparatus 100 according to the present embodiment is intended to prevent a rotational Brownian motion to align the directions of the magnetic moments 400 in the magnetic particle antibodies 303 (magnetic particles 321) with each other. To this end, with the directions of the magnetic moments 400 aligned with each other, it is necessary to define such an intensity as not to obstruct a translational motion of the magnetic particle antibodies 303 and not to cause flocculation of the magnetic particle antibodies 303. For example, when a magnetic field of an intensity $H_r$ is applied to the magnetic particle antibodies 303 in the solution, a magnetization characteristic $L(x)$ of the magnetic particles 321 in the magnetic particle antibodies 303 can be expressed with the Langevin function defined by the following expression (1).

$$L(x)=coth(x)-(1/x) \quad (1)$$

Herein, a parameter x is defined by the following expression (2), from a magnitude m of the magnetic moment 400 in the magnetic particle 321, the intensity $H_r$ of the magnetic field, the Boltzmann constant $k_B=1.38\times10^{-23}$, and a temperature T.

$$x=(mH_r)/(k_BT) \quad (2)$$

Herein, the magnetization characteristic, which is obtained when the magnetic field of the intensity $H_r$ is applied to the magnetic particle antibodies 303 (magnetic particles 321) in the solution, depends on a value of the parameter x in the expression (1) and the expression (2). For example, a lower limit of the intensity of a magnetic field to be applied in the first magnetic field 501 is defined when the value of the parameter x meets the condition of the following expression (3).

$$x>1 \quad (3)$$

Figure 6:
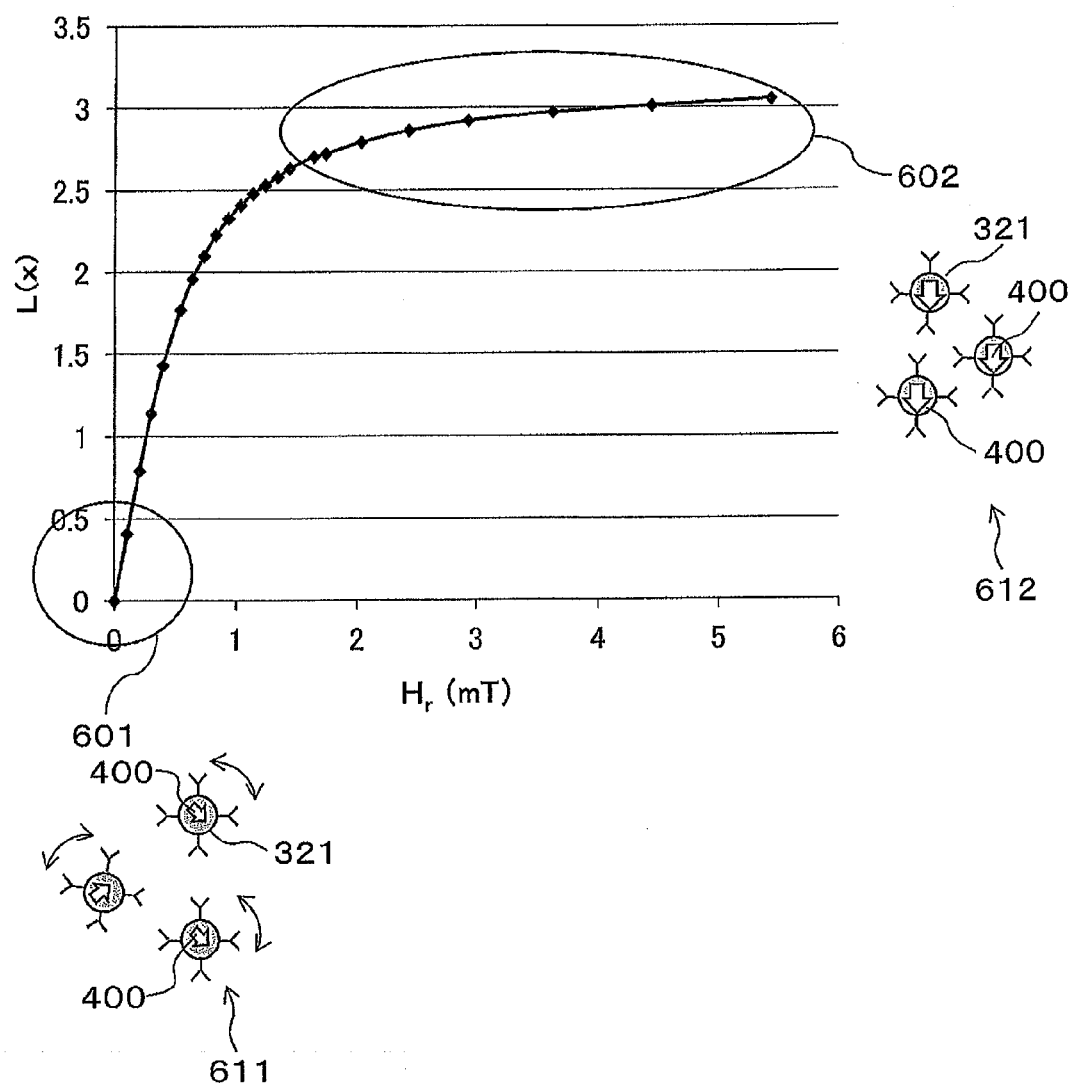
FIG. 6 is a graph representing a relationship between the intensity $H_r$ of an applied magnetic field and the magnetization characteristic $L(x)$.

FIG. 6 is a graph representing a relationship between the intensity $H_r$ of an applied magnetic field and the magnetization characteristic $L(x)$.

The magnetization characteristic $L(x)$ is defined using the Langevin function defined by the expression (1).

In FIG. 6, the abscissa axis of the graph indicates the intensity $H_r$ (unit: mT) of an applied magnetic field, and the ordinate axis indicates the magnetization characteristic $L(x)$.

For example, when the magnitude m of the magnetic moment 400 in the magnetic particle antibody 303 is $1.6\times10^{-17}$ (Am$^2$), in a region 601 which is under conditions that the intensity $H_r$ of the magnetic field is lower than 1 mT, the magnetic particle antibodies 303 make a rotational Brownian motion as indicated by reference sign 611, thereby allowing the directions of the magnetic moments 400 to become random.

On the other hand, in a region 602 which is under conditions that the intensity $H_r$ of the magnetic field is higher than 1 mT, the magnetic particle antibodies 303 make no rotational Brownian motion as indicated by reference sign 612, thereby allowing the magnetic moments 400 to align with each other in one direction to cause a translational motion.

More specifically, when the condition for the magnitude m of the magnetic moment 400 in the magnetic particle antibody 303 is $1.6\times10^{-17}$ (Am$^2$), it is when the intensity of an externally-applied magnetic field is higher than 1 mT that the magnetic moments 400 in the magnetic particle antibodies 303 can be maintained with those aligned with each other. Therefore, when the magnitude m of the magnetic moment 400 is $1.6\times10^{-17}$ (Am$^2$), the lower limit of the first magnetic field 501 is 1 mT.

Next, a description will be given of an upper limit of the intensity of a magnetic field to be applied in the second magnetic field 502.

When the magnetic field is applied to the magnetic particle antibodies 303 in the solution, the directions of the magnetic moments 400 in the magnetic particle antibodies 303 (magnetic particles 321) can be aligned in the same direction as that of the magnetic field. At this time, neighboring magnetic particle antibodies 303 are subjected to an attractive force exerted thereon, so as to bind to each other to cause flocculation. Herein, binding energy $U_m$ is defined by the following expression (4), from a vacuum magnetic permeability $\mu_0$, the magnitude m of the magnetic moment 400, and a distance d between the neighboring magnetic particle antibodies 303.

$$U_m=-\mu_0m^2/2\pi d^3 \quad (4)$$

For example, when a value of the binding energy $U_m$ increases as compared to thermal noise energy $P_n$ where a diameter $\Phi$ of the magnetic particle antibody 303 is equal to the distance d between the magnetic particles, the magnetic particle antibodies 303 are easy to bind to each other to cause flocculation thereof. Note that the thermal noise energy $P_n$ is defined by the following expression (5), from the Boltzmann constant $k_B=1.38\times10^{-23}$, and the temperature T.

$$P_n=k_BT \quad (5)$$

Accordingly, the upper limit of a magnetic field by which the magnetic particle antibodies 303 can be prevented from flocculating with each other is defined by the condition of the following expression (6).

$$U_m/P_n=U_m/(k_BT)<1 \quad (6)$$

Figure 7:
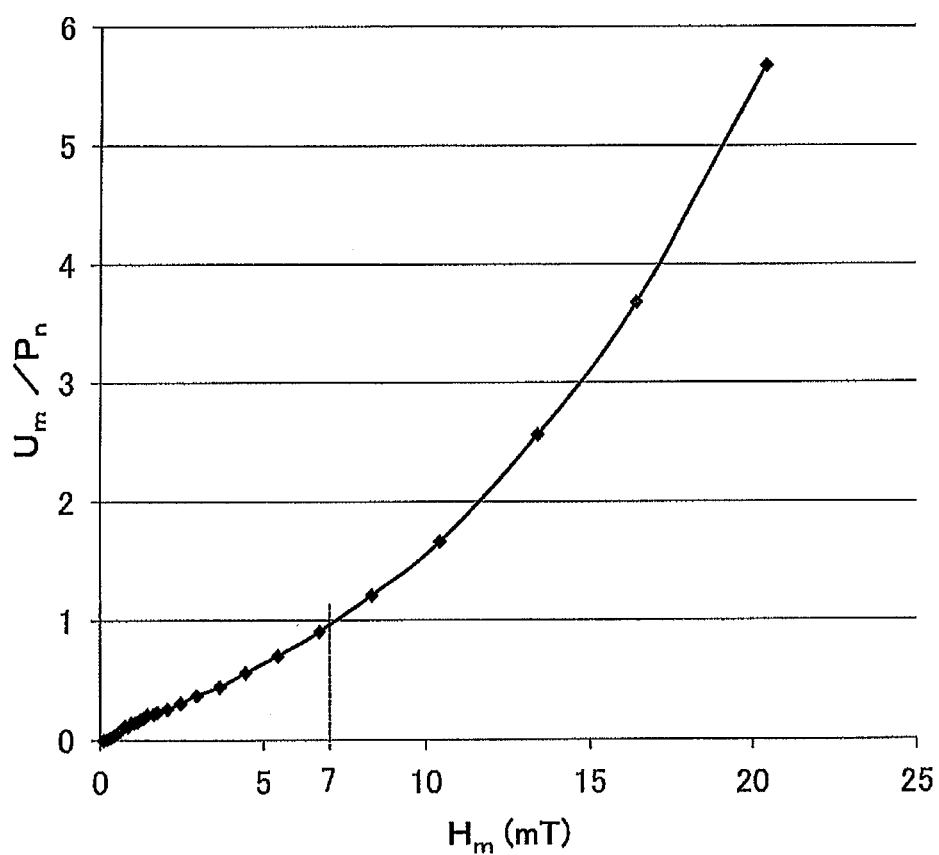
FIG. 7 is a graph representing a relationship of the ratio of a value of binding energy $U_m$ to a value of thermal noise energy $P_n$, relative to the intensity of an externally-applied magnetic field.

FIG. 7 is a graph representing a relationship of the ratio of a value of binding energy $U_m$ to a value of thermal noise energy $P_n$, relative to the intensity of an externally-applied magnetic field.

In FIG. 7, the abscissa axis indicates the intensity $H_m$ (unit: mT) of an externally-applied magnetic field, and the ordinate axis indicates the ratio ($U_m/P_n$) of the binding energy $U_m$ to the thermal noise energy $P_n$.

For example, when the diameter of the magnetic particle 321 is 270 nm, the ratio of the binding energy $U_m$ to the thermal noise energy $P_n$ is as shown in the graph of FIG. 7.

As shown in FIG. 7, when the ratio of $U_m/P_n$ meets the condition ($U_m/P_n<1$) of the expression (6), the value of the magnetic field is about 7 mT. Therefore, when the diameter of the magnetic particle 321 is 270 nm, the upper limit of the magnetic field is about 7 mT.

Thus, the upper limit of the second magnetic field 502 is generally determined based on the graph which has been prepared based on the ratio ($U_m/P_n$) of the binding energy $U_m$ to the thermal noise energy $P_n$, and the intensity $H_m$ of the magnetic field.

[Actual Measurement Results]

Next, results of a magnetic signal measurement by the magnetic signal measuring system 1 according to the present embodiment will be demonstrated with reference to FIG. 8. Reference to FIGS. 3A to 3F will be made as appropriate.

Herein, the liquid sample 300 described below was used to perform a magnetic signal measurement. As the magnetic particles 321, those commercially available (from R&D Systems Inc.) for use in cell separation were used. Also, fixed to the surface of each magnetic particle 321 is streptavidin as a substitute of the second antibody 322. Moreover, a biotin molecule was used as a measured substance and biotin beads (particle diameter: 3.3 μm, Spherotech, Inc.) were used in each of which biotin molecules were preliminarily fixed onto the bead carrier 302. Accordingly, any substance corresponding to the first antibody 311 in FIGS. 3A to 3F, 5A and 5B is not used herein. Note that the biotin molecule has a property of binding strongly to the streptavidin.

The biotin beads were diluted in a buffer solution to be 0 to $2 \times 10^5$/well. Next, the magnetic particle antibodies 303 and the biotin beads were mixed with each other and the first magnetic field 501 (0.5 mT) was applied while a binding reaction between the magnetic particle antibodies 303 and the biotin beads was being performed. Then, the second magnetic field 502 (1 mT) was applied to the liquid sample 300 which was subjected to the binding reaction, so as to magnetize the magnetic particle antibodies 303, and thereafter a magnetic signal was obtained by the SQUID 101.

Note that the conditions for the magnetic fields adopted n this experiment are ones calculated using the expressions (1) to (6) described above, based on the magnetization characteristic of the magnetic particle antibodies 303 employed.

On the other hand, as a control experiment of the present embodiment, a magnetic signal measurement by a commonly-used method in which a magnetic field is applied only once was performed.

In the commonly-used method, the same biotin beads as used in the experiment of the present embodiment and the magnetic particle antibodies 303 were mixed with each other under the same conditions as in the experiment of the present embodiment, and the liquid sample 300 with the first magnetic field not applied thereto was produced to perform a binding reaction. Next, a magnetic field (60 mT) was applied to the liquid sample 300 to magnetize the magnetic particle antibodies 303. Then, a magnetic signal was measured by the SQUID 101.

FIG. 8 is a graph representing measured results based on each of measuring methods.

In FIG. 8, the ordinate axis indicates the intensity of a magnetic signal measured, and the abscissa axis indicates the number of biotin beads.

In FIG. 8, a line 802 represents a measured result obtained by the commonly-used method, and a line 801 represents a measured result obtained by the method based on the present embodiment.

In the commonly-used method, a blank value which is a measured value obtained when the number of biotin beads is 0 exhibits a high value of about 6 $m\Phi_0$. On the other hand, in the method based on the present embodiment, the blank value exhibits a low value of about 0.8 $m\Phi_0$ and becomes diminished to about one-eighth as compared to the commonly-used method.

Moreover, a magnetic signal intensity obtained when the number of biotin beads is $2 \times 10^5$ is about 18 $m\Phi_0$ in the commonly-used method, while it is about 12 $m\Phi_0$ in the method based on the present embodiment. However, when the respective blank values are subtracted from the respective magnetic signals, both signals become about 12 $m\Phi_0$ and thus absolute values of the intensities of the respective magnetic signals are substantially unchanged. That is, the magnetic signal measuring method according to the present embodiment can provide a precise measurement even in the range other than the portion at which the number of biotin beads is 0.

It is understood from the above that the measuring method based on the present embodiment makes it possible to decrease the blank value and to detect a magnetic signal from the liquid sample 300 without decreasing it.

According to the present embodiment, the magnetic field is applied to the magnetic particle antibodies 303 in the liquid sample 300, at two stages as described below.

(1) First, when the measured substances are binding to the magnetic particle antibodies 303, the first magnetic field 501, which has an intensity of such a degree that the directions of the magnetic moments 400 in the magnetic particles 321 constituting the magnetic particle antibodies 303 can be aligned with each other, is applied to the magnetic particle antibodies 303. This makes it possible to form the complex 351 with the directions of the magnetic moments 400 in the magnetic particle antibodies 303 (magnetic particles 321) aligned with each other. Thus, the directions of the magnetic moments 400 are aligned with each other, thereby making it possible, in a magnetic signal measurement to be performed later, to facilitate the measurement of a magnetic signal and improve a measurement accuracy of the magnetic signal.

Moreover, since the first magnetic field 501 has an intensity of such a degree that the magnetic particle antibodies 303 do not flocculate with each other, redundant magnetic particle antibodies 303 do not flocculate with each other and thus do not form the complex 351.

(2) Next, the second magnetic field 502, which has an intensity of such a degree that the magnetic signal can be obtained, is applied to the magnetic particle antibodies 303. This makes it possible to measure the magnetic signal derived from the magnetic particle antibodies 303 which form the complexes 351. Herein, the second magnetic field 502 has an intensity of such a degree that the magnetic particle antibodies 303 (magnetic particles 321) do not flocculate with each other. This prevents redundant magnetic particle antibodies 303 which do not form the complex 351 from flocculating with each other. Accordingly, it is possible to decrease a blank value of a magnetic signal derived from redundant magnetic particle antibodies 303 flocculating with each other.

Also, the intensity of the first magnetic field 501 can be properly set by defining the lower limit of the intensity of the first magnetic field 501 based on the expressions (1) to (3).

Moreover, the intensity of the second magnetic field 502 can be properly set by defining the upper limit of the intensity of the second magnetic field 502 based on the expressions (4) to (6).

Furthermore, using the liquid sample 300 as a sample makes it possible to perform a magnetic measurement in a short time because the need for drying process is eliminated and to provide the magnetic signal measuring system 1 most suitable for an immunological test.

Modified Example

Since the present embodiment has been described with respect to the magnetic immunological test in which detection of a protein is performed, as shown in FIGS. 3A to 3F, the measured substance is the antigen 301 and the substances which are fixed to the bead carrier 302 and the magnetic particle antibody 303 and bind specifically to the antigen 301 are the first antibody 311 and the second antibody 322, respectively. As a modified example of the present embodiment, a measured substance may be an antibody and substances which are fixed to a magnetic particle antibody and a bead carrier and bind specifically to the antibody may be antigens. Moreover, the present embodiment can be modified as a binding test between a magnetic particle antibody and a bead carrier using a specific and selective binding for a low-molecular substance and a nucleic-acid substance other than the protein. For example, a composition may be adopted in which a receptor contained in a measured substance is fixed with a ligand such as a medical agent as a binding substance to a magnetic particle antibody and a bead carrier. Moreover, when the measured substance is a biotin, or when a biotin is bound to the measured substance, a composition may be adopted in which the measured substance is fixed with streptavidin or neutravidin as a binding substance to a magnetic particle antibody and a bead carrier.

Moreover, the present embodiment uses the sandwich binding reaction by which the measured substances in the solution are bound to two types of binding substances (the first antibody 311 and the second antibody 322) fixed to the bead carrier 302 and the magnetic particle antibody 303, respectively, so as to perform detection of the measured substances. Other than the sandwich binding reaction using the bead carrier 302 and the two types of binding substances, another binding reaction such as shown in FIGS. 9A to 9D can also be used.

FIGS. 9A to 9D are views schematically showing a reaction in a modified example in which magnetic particle antibodies are mutually flocculated with measured substances lying therebetween. FIG. 9A is a schematic view showing a state within the well 112; FIG. 9B is an enlarged schematic view showing a magnetic particle antibody to which a binding substance is bound; FIG. 9C is an enlarged schematic view showing the binding substance; and FIG. 9D is an enlarged schematic view showing a measured substance.

For example, when a low-molecular substance or a nucleic-acid substance is used as the measured substance, a molecular weight thereof is low and thus there is no more than one site which is recognized by a plurality of binding substances. To cope with this, as shown in FIGS. 9A to 9D, added to a liquid sample 300a are magnetic particle antibodies 911 each having a composition in which one type of binding substance 921 able to bind specifically to a measured substance 901 is fixed to a magnetic particle 922. In this case, although the bead carrier 302 (see FIG. 3B) is not employed, the magnetic particle antibodies 911 bind to each other via measured substances 901 to form a complex 931 containing the magnetic particle antibodies 911. The magnetic particle antibodies 911 composed as the complex 931 have remanent magnetism based on application of the magnetic field because a rotational Brownian motion thereof becomes slow. This allows a magnetic signal to be detected.

The magnetic signal detecting method shown in FIGS. 9A to 9D is the same as the method by the magnetic signal measuring apparatus shown in FIG. 2. This makes it possible to detect a substance other than a protein having a high molecular weight.

The magnetic signal measuring method implemented in the embodiment and the modified example described above requires the application of magnetic fields by the magnetic field applying unit 108, and as the magnetic field applying unit 108, an electromagnet coil can be used, or a magnet can be used. For example, when an electromagnet coil is used, ON/OFF (application or shutoff) of the first magnetic field and the second magnetic field is performed by ON/OFF (flowing or shutoff) of a current to be input to the electromagnet coil. On the other hand, when a magnet is used, the ON/OFF of the first magnetic field and the second magnetic field is performed by movement of the magnet.

The present invention is not limited to the above embodiment, but may include various modified examples. For example, the above embodiment has been described in detail in order to easily understand the present invention, but the present invention is not necessarily limited to an embodiment including all the configurations described above.

Also, the functions which the control device 200 has may be implemented with hardware, for example, by designing some or all of the functions with integrated circuits. Moreover, each of the functions in the control device 200 may be implemented with software based on which a processor such as a CPU (Central Processing Unit) interprets and executes programs for implementing the respective functions. Information on the programs for implementing each function, tables, files and the like can be stored in a recording device such as a memory or an SSD (Solid State Device), or in a recording medium such as an IC (Integrated Circuit) card, an SD (Secure Digital) card or a DVD (Digital Versatile Disc), other than being stored in an HDD (Hard Disk Drive).

In addition, each of the embodiments shows control lines and information lines which are considered necessary for explanation, but in terms of a product, does not necessarily show all of the control lines and the information lines. In fact, almost all configurations may be considered to be connected with each other.

DESCRIPTION OF REFERENCE SIGNS

1: Magnetic signal measuring system, 100: Magnetic signal measuring apparatus, 101: SQUID (Measurement unit), 106: Sample container, 107: Rotating mechanism, 108: Magnetic field applying unit, 112: Well, 141: First magnetic field applying unit, 142: Second magnetic field applying unit, 300: Liquid sample, 301: Measured substance (Substance to be measured), 302: Bead carrier, 303: Magnetic particle antibody (Magnetic substance), 311: First antibody, 321: Magnetic particle (Magnetic substance), 322: Second antibody, 501: First magnetic field, 502: Second magnetic field

What is claimed is:
1. A magnetic signal measuring apparatus comprising:
a first magnetic field applying unit that is arranged to apply a first magnetic field to a sample in which a plurality of magnetic substances and a measured substance able to bind to the magnetic substances are mixed together in an unbound state, the first magnetic field having an intensity of such a degree that the magnetic substances do not flocculate with each other and such a degree that directions of magnetic moments in the magnetic substances can be aligned with each other;
a second magnetic field applying unit that is arranged to apply a second magnetic field to the magnetic substances to which the first magnetic field has been applied, the second magnetic field having an intensity of such a degree that the magnetic substances do not flocculate with each other and such a degree that a magnetic signal can be obtained from the magnetic substances; and a measurement unit that is arranged to measure the magnetic signal derived from the magnetic substances.

2. The magnetic signal measuring apparatus according to claim 1, wherein the intensity $H_r$ of the first magnetic field has a lower limit which is defined by the following expression (1):

$$(mH_r)/(k_B T) > 1 \qquad (1)$$

where m indicates a magnitude of a magnetic moment of the magnetic substance; $H_r$ indicates the intensity of the magnetic field; $k_B = 1.38 \times 10^{-23}$ indicates the Boltzmann constant; and T indicates a temperature.

3. The magnetic signal measuring apparatus according to claim 1, wherein the intensity of the second magnetic field has an upper limit which meets a value of $U_m/P_n$ defined by the following expression (2):

$$U_m/P_n < 1 \qquad (2)$$

where $U_m$ is defined by the following expression (3) and $P_n$ is defined by the following expression (4):

$$U_m = -\mu_0 m^2 / 2\pi d^3 \qquad (3)$$

$$P_n = k_B T \qquad (4)$$

where $\mu_0$ indicates a vacuum magnetic permeability; m indicates a magnitude of a magnetic moment of the magnetic substance; d indicates a distance between the magnetic substances; $k_B = 1.38 \times 10^{-23}$ indicates the Boltzmann constant; and T indicates a temperature.

4. The magnetic signal measuring apparatus according to claim 1, wherein the sample is a liquid sample in which the magnetic substances and the measured substance exist in a solution.

5. A magnetic signal measuring method implemented by a magnetic signal measuring apparatus that measures a magnetic signal derived from a plurality of magnetic substances binding to a measured substance, the magnetic signal measuring method comprising:

applying a first magnetic field to a sample in which the magnetic substances and the measured substance are mixed together in an unbound state, the first magnetic field having an intensity of such a degree that the magnetic substances do not flocculate with each other and such a degree that directions of magnetic moments in the magnetic substances can be aligned with each other;

applying a second magnetic field to the magnetic substances to which the first magnetic field has been applied, the second magnetic field having an intensity of such a degree that the magnetic substances do not flocculate with each other and such a degree that the magnetic signal can be obtained from the magnetic substances; and measuring the magnetic signal derived from the magnetic substances.

6. The magnetic signal measuring method according to claim 5, wherein the intensity $H_r$ of the first magnetic field has a lower limit which is defined by the following expression (1):

$$(mH_r)/(k_B T) > 1 \qquad (1)$$

where m indicates a magnitude of a magnetic moment of the magnetic substance; $H_r$ indicates the intensity of the magnetic field; $k_B = 1.38 \times 10^{-23}$ indicates the Boltzmann constant; and T indicates a temperature.

7. The magnetic signal measuring method according to claim 5, wherein the intensity of the second magnetic field has an upper limit which meets a value of $U_m/P_n$ defined by the following expression (2):

$$U_m/P_n < 1 \qquad (2)$$

where $U_m$ is defined by the following expression (3) and $P_n$ is defined by the following expression (4):

$$U_m = -\mu_0 m^2 / 2\pi d^3 \qquad (3)$$

$$P_n = k_B T \qquad (4)$$

where $\mu_0$ indicates a vacuum magnetic permeability; m indicates a magnitude of a magnetic moment of the magnetic substance; d indicates a distance between the magnetic substances; $k_B = 1.38 \times 10^{-23}$ indicates the Boltzmann constant; and T indicates a temperature.

8. The magnetic signal measuring method according to claim 5, wherein the sample is a liquid sample in which the magnetic substances and the measured substance exist in a solution.

* * * * *